(12) United States Patent
Mateu et al.

(10) Patent No.: US 8,999,308 B2
(45) Date of Patent: Apr. 7, 2015

(54) TWO-PART COSMETIC PRODUCT WITH VOLUMIZING EFFECT TO HAIR FIBERS

(75) Inventors: Juan R. Mateu, Oak Ridge, NJ (US); Salvatore J. Barone, Staten Island, NY (US); Ralph Macchio, Sparta, NJ (US)

(73) Assignee: Coty Germany GmbH, Mainz (DE)

( * ) Notice: Subject to any disclaimer, the term of this patent is extended or adjusted under 35 U.S.C. 154(b) by 883 days.

(21) Appl. No.: 12/681,571

(22) PCT Filed: Oct. 2, 2008

(86) PCT No.: PCT/EP2008/063204
§ 371 (c)(1),
(2), (4) Date: Oct. 1, 2010

(87) PCT Pub. No.: WO2009/043898
PCT Pub. Date: Apr. 9, 2009

(65) Prior Publication Data
US 2011/0014249 A1    Jan. 20, 2011

(30) Foreign Application Priority Data
Oct. 5, 2007    (EP) .................................... 07117999

(51) Int. Cl.
| | |
|---|---|
| *A61Q 1/10* | (2006.01) |
| *A61K 8/19* | (2006.01) |
| *A61K 8/81* | (2006.01) |
| *A61K 8/87* | (2006.01) |
| *A61K 8/892* | (2006.01) |
| *A61K 8/92* | (2006.01) |
| *A61Q 5/00* | (2006.01) |
| *A61K 8/26* | (2006.01) |
| *A61K 8/34* | (2006.01) |

(52) U.S. Cl.
CPC ... *A61Q 1/10* (2013.01); *A61K 8/19* (2013.01); *A61K 8/26* (2013.01); *A61K 8/345* (2013.01); *A61K 8/8152* (2013.01); *A61K 8/87* (2013.01); *A61K 8/892* (2013.01); *A61K 8/927* (2013.01); *A61Q 5/00* (2013.01); *A61K 2800/31* (2013.01); *A61K 2800/88* (2013.01); *A61K 2800/884* (2013.01)

(58) Field of Classification Search
CPC   A61Q 1/10; A61K 2800/88; A61K 2800/884
USPC .......................................................... 424/401
See application file for complete search history.

(56) References Cited

U.S. PATENT DOCUMENTS

| | | | |
|---|---|---|---|
| 2005/0089498 A1* | 4/2005 | Patil et al. ................ | 424/70.122 |
| 2006/0147399 A1 | 7/2006 | McNamara et al. | |
| 2006/0216257 A1 | 9/2006 | Pays et al. | |
| 2007/0212316 A1* | 9/2007 | Feng et al. .................. | 424/70.7 |

FOREIGN PATENT DOCUMENTS

| | | |
|---|---|---|
| DE | 19817522 | 10/1999 |
| EP | 1704896 | 9/2006 |

* cited by examiner

*Primary Examiner* — Rachael E Bredefeld
(74) *Attorney, Agent, or Firm* — Novak Druce Connolly Bove + Quigg LLP

(57) ABSTRACT

The present invention relates to a two-part cosmetic product that imparts a filling and/or swelling effect to hair, eyebrows or eyelashes, preferably a mascara. The invention uses an anhydrous base coat composition with a water absorbing ingredient being a salt of acrylic or polyacrylic acid and a $CO_2$ releasing compound which is a carbonate or bicarbonate to expand or swell the film former of the top coat with the in situ generated $CO_2$ when the water containing top coat is applied to the anhydrous base coat.

10 Claims, No Drawings

TWO-PART COSMETIC PRODUCT WITH VOLUMIZING EFFECT TO HAIR FIBERS

CROSS-REFERENCE TO RELATED APPLICATIONS

This application is a §371 national stage entry of International Application No. PCT/EP2008/063204, filed Oct. 2, 2008, which claims priority to European Patent Application 07 117 999.8, filed Oct. 5, 2007, the entire contents of which are incorporated herein by reference.

FIELD OF THE INVENTION

The present invention relates to a two-part cosmetic product that imparts a filling and/or swelling effect to hair, eyebrows or eyelashes, preferably a mascara. The swelling effect is based on expansion with in situ generated $CO_2$. The invention uses an anhydrous base coat composition with a water absorbing ingredient being a salt of acrylic or polyacrylic acid and a $CO_2$ releasing compound which is a carbonate or bicarbonate to expand or swell the film former of the top coat with the in situ generated $CO_2$ when the water containing top coat is applied to the anhydrous base coat.

BACKGROUND OF THE INVENTION

For many cosmetic formulations it is desirable to provide volumizing effect to hair, eyelashes and/or eyebrows. Especially mascaras are used to achieve expansion of eyelashes or eyebrows.

US 2006/0147399A1 discloses post-application expanding compositions for application to hair, eyelashes or eyebrows that use in situ generated $CO_2$ to foam one or more surfactant components of the composition. A film-forming component of the composition is used to entrap at least a portion of the foam lattice and, when set, fix the composition in an expanded state. This two-part system which is described on pages 18 to 21 of the above application uses an anhydrous carbonate or bicarbonate and an anhydrous acid, preferably citric acid, in an anhydrous mascara composition which is mixed on the eyelashes with an aqueous top composition containing the surfactant and preferably the film forming agent. The $CO_2$ which is produced acts to foam the surfactant and the solvent for the surfactant. When the film-forming agent, which is preferably present in the aqueous solution sets, it entraps the produced foam or a portion thereof. To suspend the anhydrous acid and base without co-reacting anhydrous polyethylene glycol, sorbitol and glycerin are the suggested solvents in the base coat of the above application. However, the resulting films are instable and the volumetric effect is short lived.

US 2006/0216257 discloses an alternative post-application expanding composition to produce a volumetric effect. That composition consists of an oily and an aqueous part wherein the oily part comprises at least one polyelectrolyte. After combination of the two parts the polyelectrolyte acts as a "water pump". The resulting film becomes hydrated and swells. However, these films dry out easily and instability issues arise. Further, the usually generated volumetric effect generated by applying a water topcoat over a water swellable film is negligible, because such films need to be mixed well. To improve the volumetric effect surfactants are added to the composition. However, a foam structure which is achieved using surfactants is very instable so that the resulting effects are short lived.

It would be desirable to have a cosmetic formulation with a long lasting volumizing effect to hair, eyebrows and eyelashes, especially a mascara, which overcome the above mentioned problems of the compositions of the prior art. The desired cosmetic formulation should provide a clear, smooth, flexible and durable film on the hair fibers which satisfies the aesthetic requirements of the consumers.

The composition should also be easy to produce in a cost-efficient manner. Due to safety concerns it also is desirable to avoid the use of aggressive conditions near the eyes, e.g. the use of citric acid.

SUMMARY OF THE INVENTION

It is an object of the present invention to provide a two-part cosmetic product for imparting swelling effects to hair fibers of the scalp, eyebrows or eyelashes.

It is another object of the present invention to provide a two-part cosmetic product in kit form, the kit comprising in different chambers of a single two chambered container or in two separate containers an anhydrous base coat composition and a water containing polymer as top coat, the base coat composition and the top coat being applied sequentially to the hair, eyebrows and/or eyelashes.

It is still another object of the present invention to provide a method for imparting swelling effects to hair, eyebrows or eyelashes by applying the two-part cosmetic product of the invention.

DETAILED DESCRIPTION

The present invention provides a two-part cosmetic product for sequential application to hair fibers of the scalp, eyebrows or eyelashes to impart a swelling effect comprising an anhydrous base coat composition and a water containing polymer as top coat, wherein a) the anhydrous base coat composition comprises at least one water absorbent compound which is a cosmetically acceptable salt of acrylic or polyacrylic acid and optionally further water absorbent compounds, a $CO_2$ releasing compound which is an inorganic or organic carbonate, or bicarbonate, a solvent for the water absorbent compound and the $CO_2$ releasing compound, a wax and auxiliary substances, wherein the solvent is an anhydrous solvent which does not allow an interaction of the salt of acrylic or polyacrylic acid and $CO_2$ releasing compound before the water containing polymer of the top coat is applied to the base coat composition and wherein the salt of acrylic or polyacrylic acid and the $CO_2$ releasing compound are contained in an amount effective to interact and generate $CO_2$ when the water containing polymer is applied
and wherein b) the water containing polymer which is a film former has a viscosity which is smaller than that of the base coat composition, and the polymer is present in the top coat in an amount effective to form a film on the hair fibers and to be expanded by $CO_2$ after application to the base coat composition.

That means, the cosmetic product of the invention has two compositional parts for sequential application to hair fibers. The base coat composition is anhydrous and comprises at least one water absorbent compound which is a salt of acrylic or polyacrylic acid, preferably polyacrylic acid. The salt is for example a sodium salt, potassium salt, ammonium salt, calcium salt or magnesium salt, preferably a sodium salt. Most preferred is sodium polyacrylate, for example Rapithix™ A-100, a personal care product of the ISP group (INCI Name:

Sodium Polyacrylate). The base coat composition comprises at about 1 to about 80 weight % of water absorbent compounds, at least said acrylic or polyacrylic salt. Preferably about 15 to about 35 weight % of water absorbent compounds, at least said acrylic or polyacrylic salt, are contained, based on the total weight of the base coat composition.

The base coat composition further comprises a $CO_2$ releasing compound which is an inorganic or organic carbonate, or bicarbonate. Inorganic carbonates or bicarbonates are for example alkali metal, alkaline earth metal or ammonium carbonates and bicarbonates. Alkali metal bicarbonates are preferred. Most preferred is sodium bicarbonate. The $CO_2$ releasing compound is present in the base coat composition at about 1 to about 80 weight % based on the total weight of the base coat composition, preferably at about 10 to about 80 weight % and more preferred at about 15 to about 35 weight %. In a most preferred embodiment more than 25 weight % of the $CO_2$ releasing compound are present in the base coat composition according to the invention.

According to the invention, the anhydrous cosmetically acceptable solvent in which the salt of acrylic or polyacrylic acid and the $CO_2$ releasing compound is suspended without co-reacting is for example a silicone compound, preferably with hydroxyl functionality, most preferred a silicone compound selected from the group comprising dimethiconol, dimethicone, cyclomethicones, phenyl trimethicone, amodimethicone and mixtures thereof, preferably dimethiconol.

According to the invention it is especially preferred to use dimethiconol in cyclomethicone silicone oil, preferably DC 1501 (Dow Corning). But also other anhydrous solvents which are used in mascara formulations like hydrocarbons, esters or vegetable oils may be applied, with the exception of anhydrous polyethylene glycol, sorbitol and glycerine which are not suitable for the cosmetic product of the invention to avoid that the release of the $CO_2$ is induced and the swelling occurs before the top coat is applied. The solvent is present in the base coat composition at about 1 to about 80 weight % based on the total weight of the base coat composition, preferably at about 20 to about 40 weight %.

The two-part composition of the present invention forms a very smooth and stable continuous film on hair fibers of the scalp, eyebrows or eyelashes which does not flake.

The base coat composition further comprises a wax which is in a preferred embodiment an emulsifying wax, most preferred PEG-8 Beeswax. The wax is present in the base coat composition at about 2 to about 6 weight %, preferably 4 weight %, based on the total weight of the base coat composition. Beside PEG-8 Beeswax natural and synthetic waxes may be contained in the base coat composition as auxiliary substances. The amount of all waxes can be up to 30 weight % based on the total weight of base coat composition.

Beside the necessary water absorbent compound of the base coat composition which is a salt of acrylic or polyacrylic acid one or more additional water absorbent compounds can be contained in the base coat which are selected from the group comprising cellulose gum, polysaccharides, natural gums, clays, aluminum silicate, bentonite, Aluminum starch octenylsuccinate, acrylic acid and polyacrylic acid.

However, these additional water absorbent compounds are not needed to achieve the volumetric effect of the invention. The volumetric effect according to the invention is based on the $CO_2$ release. $CO_2$ bubbles are entrapped by the film forming agent of the top coat composition which does not infiltrate into the base coat composition. Thus, the top coat composition swells maximally. A moderate additional volume increase is achieved by the use of the water absorbing compound which is also the acidic agent of the invention. Thus, the $CO_2$ release is achieved without the use of acid solutions and the formation of salts with no structural strength which is avoided crumble into powder when touched.

According to the invention a volume effect of at least 6 times original lash volume preferably of at least 8 times is achieved. If the above mentioned additional water absorbing compounds are also combined in the base coat composition the volumetric effect may be further increased.

The auxiliary substances of the base coat composition according to the invention are selected from the group comprising natural and synthetic waxes, colorants, fillers, preservatives and hair care extracts which are selected from the usual compounds being contained in a mascara. According to the invention surfactants or other foaming compounds, such as highly volatile agents, are excluded from the auxiliary substances.

Suitable natural waxes are for instance Beeswax, preferably PEGS-Beeswax, carnauba wax, candelilla wax. Suitable synthetic waxes are for instance polyethylene, ozokerite, mineral waxes or emylsifying waxes. Suitable preservatives are for instance parabens, phenoxyethanol, Caprylyl Glycol or any typical preservative used in the personal care/cosmetic industry.

If it is intended to impart a color to hair fibers, the colorates which may be contained in the base coat composition are preferably pigments, for instance iron (II, III) oxide, titanium dioxide, manganese violet, copper powder, bismuth oxychloride, bronze powder. The colorant is present in an amount sufficient to impart a color to the hair fiber on which it is applied. The base coat composition of the invention includes about 1 to about 20 weight % colorant (based on the total weight of the base coat composition), preferably 3 to 15 weight %, most preferred 5 to 10 weight %.

The base coat composition contains about 1 to about 50 weight % fillers, for example mica, talc and other usual mascara fillers. In a preferred embodiment the fillers are contained from about 5 to about 20 weight %.

In an especially preferred embodiment of the invention the base coat composition comprises sodium bicarbonate, sodium polyacrylate, dimethiconol in cyclomethiconol silicone oil, iron oxide, optionally mica, PEG-8-Beeswax and a preservative.

The described base coat composition is applied to the hair fibers first and then the water containing polymer of the top coat is applied over the base coat to introduce water into the base coat composition which effects both the swelling of the water absorbent in the base coat and the $CO_2$-generation by reaction of the carbonate or bicarbonate with the acid of the salt of acrylic or polyacrylic acid. According to the invention the generated $CO_2$ is entrapped by the top coat composition and does not diffuse into the atmosphere. The top coat sets onto to base coat and is inflated by the generated $CO_2$. The dried film according to the invention can be described as a gas filled dome over the base coat composition.

According to the invention the water containing polymer has a viscosity which is smaller than that of the base coat composition, preferably from about 0.001 to about 10 Pa·s, most preferred from about 0.1 to about 0.5 Pa·s. The polymer contains at least 60 weight % water, based on the total weight of the water containing polymer. The polymer itself is contained from about 10 to about 80 weight %, preferably from about 25 to about 35 weight %, most preferred of about 30 weight %, based on the total weight of the water containing polymer.

The water containing polymer is a film former selected from the group comprising a polyurethane, a water soluble polyester, an acrylate copolymer, a methacrylate copolymer, an acrylamide, an acrylamide copolymer, PVP, PVP copolymer, chitosan, a chitosan copolymer, a polyquaternium, and mixtures of these film formers. A polyurethane is an especially preferred material, particularly Luviset®P.U.R. (BASF Aktiengesellschaft) (INCI Name: Polyurethane-1). This material consists of 30% polyurethane, 10% ethanol and 60% water, based on the total weight of this water containing polymer. To use the other water containing polymers described above for the purpose of the present invention it is important that they have a water content of at least 60 weight %, based on the total weight of the water containing polymer, or that their water content is enhanced to at least 60 weight % before using them as top coat according to the present invention. Another preferred water containing polymer according to the invention is Polyester-5, trade name Eastman AQ™ 55SPolymer.

The base coat composition of the invention is prepared by heating the solvent, the wax(es) and the preservative(s) to about 80° C. and mixing them until homogenous. Then the colorant, the fillers, the carbonate and the salt of the acrylic or polyacrylic acid are added in this order at 80° C.

The preferably used Polyurethane-1 has the advantage that it is both a film former and an expandable compound. It provides a clear and flexible film which is expandable with $CO_2$ and which remains intact after expansion so that no flaking occurs. The film remains externally on the hair fibers and can only be removed with warm water. Because of the low viscosity of Polyurethane-1 from 100 to 400 mPa·s the ease of application is enhanced, that means, the application can be done quickly.

According to the invention the salt of polyacrylic or acrylic acid in the base coat composition has also two functions. First, it absorbs the water and swells once the water-containing polymer of the top coat is applied over the base coat. Second, it dissociates to produce acrylic or polyacrylic acid once water is introduced.

It is also advantageous for the consumers that the colorant, if any, is contained in the base coat. So the color coating can be applied to consumers satisfaction without inducing the $CO_2$ generation. Due to the higher viscosity of the base coat composition compared to the top coat composition the application of the base coat is very easy and a great amount of the composition adheres to the hair fibres during one application procedure.

EXAMPLES

The following examples are offered to illustrate the two-part cosmetic products of the present invention. They are not intended to be limiting in any respect.

Example 1

A mascara is prepared which contains in the base coat composition

| | |
|---|---|
| 25 weight % | Sodium bicarbonate |
| 25 weight % | Rapithix A-100 (Sodium Polyacrylate) |
| 30 weight % | DC 1501 |
| 7.3 weight % | Iron oxide |
| 8 weight % | Mica |
| 4 weight % | PEG8-Beeswax |
| 0.7 weight % | Caprylyl Glycol (Inolex Lexgard 0) |

The weight % are based on the total weight of the base coat composition.

The base coat composition is prepared by heating DC 1501, PEG8-Beeswax and the preservative Caprylyl Glycol up to 80° C. and mixing them until homogenous. Then the iron oxide, mica, sodium bicarbonate and Rapithix A-100 are added in this order at 80° C.

The top coat composition is Polyurethane-1.

Example 2

A mascara is prepared as shown in Example 1. The base coat composition contains

| | |
|---|---|
| 26 weight % | Sodium bicarbonate |
| 25 weight % | Rapithix A-100 (Sodium Polyacrylate) |
| 29 weight % | DC 1501 (Cyclopentasiloxane and Dimethiconol) |
| 7.3 weight % | Iron oxide |
| 8 weight % | Mica |
| 4 weight % | PEG8-Beeswax |
| 0.7 weight % | Caprylyl Glycol (Inolex Lexgard 0) |

The weight % are based on the total weight of the base coat composition.

The top coat composition is Polyurethane-1.

Example 3

A mascara is prepared which contains in the base coat composition

| | |
|---|---|
| 29 weight % | Sodium bicarbonate |
| 25 weight % | Rapithix A-100 (Sodium Polyacrylate) |
| 5.3 weight % | Dimethiconol |
| 18 weight % | Cyclomethicone |
| 18 weight % | Black Iron oxide |
| 4 weight % | PEG8-Beeswax |
| 0.7 weight % | Caprylyl Glycol (Inolex Lexgard 0) |

The weight % are based on the total weight of the base coat composition.

The base coat composition is prepared by heating Dimethiconol, Cyclomethicone, PEGS-Beeswax and the preservative Caprylyl Glycol up to 80° C. and mixing them until homogenous. Then the black iron oxide, sodium bicarbonate and Rapithix A-100 are added in this order at 80° C.

The top coat composition is Polyurethane-1.

Example 4

Application of the Mascara of Example 1

The base coat of Example 1 is applied to eye lashes and three minutes are necessary for film to set. Then the top coat of Example 1 is applied. Swelling is immediately noticeable. The volume effect achieved up to 8 times original lash volume.

Example 5

Standard false eyelashes made from 100 percent human hair (elegant eyelashes) were used to show the volumetric effect according to the invention. Eyelashes are approximated as equal solid cylinders. Volume was calculated measuring the length and the radius of the eyelash using the microscopes reticle (relative values). The radius was measured at three different points along the length of the eyelash. Values are averaged and the volume was calculated. Then the eyelash was treated with the cosmetic formulation of Example 2.

Values for length and radius were measured as described before. Volume analysis was done before and after second application of the top coat. The untreated eyelash has a volume of 5.7. After application of the cosmetic composition a volume of 50.9 was measured. Thus, the volume of the eyelash has increased 9 times compared to the original volume applying the two-part cosmetic product according to the invention.

The invention claimed is:

1. A two-part cosmetic product for sequential application to hair fibers of the scalp, eyebrows or eyelashes to impart a swelling effect consisting of an anhydrous base coat composition and a top coat wherein
   a) the anhydrous base coat composition consists of:
      i.) at least one water absorbent compound which is a cosmetically acceptable salt of acrylic or polyacrylic acid,
      ii.) a $CO_2$ releasing compound which is an inorganic or organic carbonate, or bicarbonate,
      iii.) a solvent for the water absorbent compound and the $CO_2$ releasing compound,
      iv.) a wax
      v.) auxiliary substances which do not encompass surfactants and
      vi.) optionally, a second water absorbent compound selected from the group consisting of cellulose gum, polysaccharides, natural gums, clays, aluminum silicate, bentonite, aluminum starch octenylsuccinate, acrylic acid, and polyacrylic acid;
      wherein the solvent is dimethiconol in cyclomethicone silicone oil and does not allow an interaction of the salt of acrylic or polyacrylic acid and $CO_2$ releasing compound before the top coat is applied to the base coat composition and wherein the salt of acrylic or polyacrylic acid and the $CO_2$ releasing compound are present in an amount effective to interact and generate $CO_2$ when the top coat is applied, wherein the amount of the salt of acrylic or polyacrylic acid is 15-35% by weight and the amount of the $CO_2$ releasing compound is 10-80% by weight, the weight % being based on the total weight of the base coat composition, and wherein
   b) the topcoat consists of a film former and water with a viscosity that is smaller than that of the base coat composition and the film former is present in the top coat in an amount effective to form a film on the hair fibers and to be expanded by $CO_2$ after application to the base coat composition.

2. The two-part cosmetic product of claim 1, wherein the film former of the top coat is selected from the group consisting of a polyurethane, an acrylate copolymer, a methacrylate copolymer, an acrylamide, an acrylamide copolymer, polyvinylpyrrolidone (PVP), polyvinylpyrrolidone (PVP) copolymer, chitosan, a chitosan copolymer, a polyquaternium, a water soluble polyester and mixtures of these film formers.

3. The two-part cosmetic product of claim 1, wherein the film former is a polyurethane.

4. The two-part cosmetic product of claim 1, wherein the film former is present in the top coat in an amount of 10 to 80 weight % based on the total weight of the top coat.

5. The two-part cosmetic product of claim 1, wherein the salt of polyacrylic acid is sodium polyacrylate.

6. The two-part cosmetic product of claim 1, wherein the wax is an emulsifying wax.

7. The two-part cosmetic product of claim 1, wherein the auxiliary substances in the base coat composition are selected from the group consisting of natural and synthetic waxes, colorants, fillers, preservatives, and hair care extracts.

8. The two-part cosmetic product of claim 1, wherein the solvent in the base coat composition is present in an amount of 1 to 80 weight %, the weight % being based on the total weight of the base coat composition.

9. The two-part cosmetic product of claim 1, wherein the $CO_2$ releasing compound is sodium bicarbonate.

10. A kit comprising a single two chambered container or two separate containers with a two-part cosmetic product for sequential application to hair fibers of the scalp, eyebrows or eyelashes to impart a swelling effect consisting of an anhydrous base coat composition and a topcoat, wherein the first container or first chamber consists of the anhydrous base coat composition and the second container or second chamber consists of the topcoat, wherein
   a) the anhydrous base coat composition consists of:
      i.) at least one water absorbent compound which is a cosmetically acceptable salt of acrylic or polyacrylic acid,
      ii.) a $CO_2$ releasing compound which is an inorganic or organic carbonate, or bicarbonate,
      iii.) a solvent for the water absorbent compound and the $CO_2$ releasing compound,
      iv.) a wax
      v.) auxiliary substances which do not encompass surfactants and
      vi.) optionally, a second water absorbent compound selected from the group consisting of cellulose gum, polysaccharides, natural gums, clays, aluminum silicate, bentonite, aluminum starch octenylsuccinate, acrylic acid, and polyacrylic acid;
      wherein the solvent is dimethiconol in cyclomethicone silicone oil and does not allow an interaction of the salt of acrylic or polyacrylic acid and $CO_2$ releasing compound before the top coat is applied to the base coat composition and wherein the salt of acrylic or polyacrylic acid and the $CO_2$ releasing compound are present in an amount effective to interact and generate $CO_2$ when the top coat is applied, wherein the amount of the salt of acrylic or polyacrylic acid is 15-35% by weight and the amount of the $CO_2$ releasing compound is 10-80% by weight, the weight % being based on the total weight of the base coat composition, and wherein
   b) the topcoat consists of a film former and water with a viscosity that is smaller than that of the base coat composition and the film former is present in the top coat in an amount effective to form a film on the hair fibers and to be expanded by $CO_2$ after application to the base coat composition.

* * * * *